(12) United States Patent
Snyder et al.

(10) Patent No.: US 6,257,076 B1
(45) Date of Patent: Jul. 10, 2001

(54) SAMPLE INJECTOR WITH PLUNGER RELEASE FOR CHEMICAL ANALYSIS SYSTEMS

(75) Inventors: Philip A. Snyder, Hayward; James Steven Fullemann, deceased, late of Half Moon Bay, both of CA (US), by Ivan Crockett, legal representative

(73) Assignee: Merlin Instrument Company, Half Moon Bay, CA (US)

( * ) Notice: Subject to any disclaimer, the term of this patent is extended or adjusted under 35 U.S.C. 154(b) by 0 days.

(21) Appl. No.: 09/237,508

(22) Filed: Jan. 26, 1999

(51) Int. Cl.$^7$ ...................................................... G01N 1/00
(52) U.S. Cl. ........................................................ 73/864.87
(58) Field of Search ........................... 73/864.87, 864.86, 73/864.21, 864.22, 864.23, 864.24, 864.25, 61.55, 61.56, 61.59, 864.81; 422/100; 222/47; 95/89

(56) References Cited

U.S. PATENT DOCUMENTS

| 3,604,269 | * | 9/1971 | Smith et al. | 73/864.87 |
| 3,754,443 | * | 8/1973 | Harris, Sr. et al. | 73/863.81 |
| 3,824,859 | * | 7/1974 | Harris, Sr. et al. | 73/864.87 |
| 4,094,197 | * | 6/1978 | Harris, Sr. et al. | 73/863.81 |
| 4,228,922 | * | 10/1980 | Takeshita | 222/47 |
| 4,440,550 | * | 4/1984 | Jenkins et al. | 95/89 |
| 5,611,784 | | 3/1997 | Baressi et al. | 604/211 |
| 5,756,905 | * | 5/1998 | Ueda | 73/864.24 |

FOREIGN PATENT DOCUMENTS

| 242286 | * | 1/1987 | (DE) | G01N/30/16 |
| 0028408 | * | 5/1981 | (EP) | G01N/31/08 |
| 0141148 | * | 5/1985 | (EP) | G01N/30/24 |
| 724931 | * | 11/1978 | (SU) | G01F/13/00 |
| 1673952 | * | 7/1989 | (SU) | G01N/30/24 |
| 1791716 | * | 1/1993 | (SU) | G01F/11/04 |

* cited by examiner

Primary Examiner—Hezron Williams
Assistant Examiner—Jay L. Politzer
(74) Attorney, Agent, or Firm—Clifton L. Anderson

(57) ABSTRACT

A manual sample injector for a gas chromatograph comprises a syringe holder, a plunger driver including a volume-adjust assembly, an injection port interface, a release lever, and a force-calibration spring. The holder, driver, and interface collectively include guide rod and respective apertures so that the driver and interface can slide vertically relative to the holder. Pre-injection steps provide that the desired volume of sample is ready for injection. Injection steps include: mounting the injector on an injection port by sliding the port interface over a septum cap of the injection port, manually pushing the plunger driver, and thus the syringe holder, down against the resistance of the force-calibration spring until an actuator element of the port interface contacts the cocked release lever, increasing the downward force on the plunger driver so that the release lever is forced to a release position. Once the release lever is in its release position, the force already being applied to the plunger driver forces the plunger down the syringe, thereby ejecting the sample into the injection port in a repeatable manner. In moving from its cocked position to its release position, the release forces the plunger driver and thus the plunger up relative to the syringe holder and thus the syringe body. This withdraws sample from the needle end so that, during sample injection, the sample has time to accelerate before exiting the syringe needle. This provides for a desired "spitting" action of the sample into the injection port.

6 Claims, 10 Drawing Sheets

SAMPLE INJECTOR WITH PLUNGER RELEASE FOR CHEMICAL ANALYSIS SYSTEMS

BACKGROUND OF THE INVENTION

The present invention relates to chemical analysis and, more particularly, to devices for injecting samples into analytical equipment. A major objective of the present invention is to provide for improved manual injection of a sample into a gas chromatography (GC) system.

The contributions of the medical, environmental and life sciences to humanity have been facilitated by advances in chemical analysis. Many analytical techniques provide for the division of a complex sample into its components. Gas chromatography is one such analytical technique that separates volatized chemical components according to their relative partitioning between a gaseous mobile phase and a stationary (typically solid) phase. The solid phase is bound within a chromatography column, through which the mobile phase flows.

In gas chromatography, components in the mobile phase flow at generally the same rate. However, components favoring the stationary phase (having a lower partitioning constant) spend less time in the mobile phase, and thus have a lower average-flow (elution) rate through the column. Due to the different elution rates, sample components separate into bands, e.g., statistical distributions about a peak, as they progress through the column.

Preferably, separation continues until overlap between bands is negligible. This facilitates detection and quantification of sample components. In addition, components can be separately collected for further analysis. In general, greater separation can be achieved using narrower-bore columns, with capillary separation columns being state-of-the-art.

Especially with capillary columns, the volume of sample introduced is critical to effective component separation. Since the diameter of the column is a given, variations in sample volume are reflected in the initial "plug" length the sample occupies in the column. The shorter the initial plug, the more narrow will be the distributions about the peaks as the components separate. A short plug and, thus, a small sample volume is desired. However, if the sample volume is too small, some components can be difficult to detect; also quantification is less certain. Accordingly, the sample volume for capillary GC columns must be both small, e.g., less than 500 nanoliters, and precisely controlled.

Generally, a large volume can be injected with greater relative precision than can be a small volume. "Split-mode" injection systems divide a relatively large volume of sample between plural sample paths so that the volume in the one path through the column is a desired smaller volume. This is an expensive and complicated solution. In addition, the splitting process can introduce undesirable discrimination among sample components; this discrimination can occur where proportionally more of one component is vented than another component so that the composition of the sample in the GC column differs from its composition in the syringe. Accordingly, it is desired to provide for smaller sample volumes upon injection to avoid split-mode injections or to allow smaller split ratios to reduce component discrimination.

Control of sample injection volume pertains, in part, to syringe design. Syringes with capacities of 5 microliters or 10 microliters are common. These syringes are typically graduated to provide for measurement of smaller volumes. However, measurement of the small volumes is subject to parallax errors, which can affect the precision of sample volume determinations.

The manner in which the sample is injected also bears on the volume of sample injected. If the sample is ejected too slowly from the syringe needle so that it "drools" out, some of the sample can wick to the outside surface of the needle and/or to an injection port septum. The wicked volume might be lost, e.g., if it exits the port with the needle instead of through the column. Even worse, the wicked volume might flow through the column after a delay relative to the main body of the sample; this confuses detections and quantifications.

This drooling effect can be minimized by ejecting the sample at a sufficiently high velocity that it forms a jet as it leaves the needle. This "spitting" action can still leave some sample on the needle. However, selecting an appropriately high velocity achieves a "clean spit" so that sample does not remain on the needle.

On the other hand, as it was discovered in the course of the present invention, the ejection velocity can be too high in which case "overspitting" occurs. Since a syringe plunger does not extend into the needle, it is normal for some volume of sample to remain in the needle after injection. If the injection velocity is excessive, a portion of this sample volume that is supposed to remain is actually injected. Accordingly, injection velocity should be sufficient to attain a clean spit but not risk overspitting.

Furthermore, the delay between the needle's insertion into a GC port and injection of the sample must be kept small. Prior to insertion, a syringe needle is typically at room temperature, while the interior of the injection port is heated sufficiently to volatilize the sample. The needle begins heating as soon as it is inserted through the injection septum. If sufficient heating occurs prior to injection, some sample in the needle can volatilize and enter the column ahead of the bulk of the sample. The leading sample volume can then confuse detection and quantification.

Autoinjectors would appear to meet most of the criteria for sample injections into a capillary GC system. They can inject a sample soon after a needle penetrates an injection septum, and they can inject with high velocities in a repeatable manner. Nonetheless, there remains a problem with repeatability when it comes to injection of very small sample volumes. However, any problems facing autoinjection are dwarfed by those facing manual sample injection.

An autoinjector may be unavailable for reasons of cost, portability, downtime, and unsuitability for a given task. In these circumstances, manual injection is an attractive and sometimes necessary alternative. However, human physical control tends to be rather gross and slow relative to the demands of capillary GC sample injection.

Consider the case where a syringe is held by hand and the plunger operated by a finger or a thumb. There are difficulties ensuring the syringe holds the proper amount of sample: there is a parallax problem in reading the graduations; and there is a manual problem of controlling the plunger with the precision to match the desired graduation. Then there is a problem with alignment with the septum. A misaligned insertion can result in a damaged needle or plunger.

Assuming an aligned insertion, there can be a delay between the time the needle penetrates the septum and the time the plunger is operated to eject the sample; in the meantime, the needle can have heated to the point that some sample is volatized and carried down the column ahead of the main sample plug.

The most difficult problem would seem to be achieving the precise sample injection velocity. There can be large variations between human operators; and even variations in the injections of an individual operator. This variability can lead to some samples being drooled in, others being spit in, but not cleanly, and others being overspit. The desired clean spit is difficult to achieve manually on a repeatable basis.

What is needed is a system that allows for precise manual sample injection in general and specifically for capillary GC systems. The injections should occur soon after needle insertion through an injection septum. A precise volume of sample should be injected at a precise "clean-spit" velocity to optimize separation effectiveness. Finally, some improvement in the handling of small sample volumes by autoinjectors is desired.

SUMMARY OF THE INVENTION

The present invention provides a sample injector having a syringe holder, a plunger driver, a release, an actuator, and a spring. The syringe holder holds a syringe body; the plunger driver holds the plunger. The syringe holder and the plunger driver are movably engaged (e.g., they slide relative to each other in the direction of the plunger movement) so that the plunger can be moved to draw sample in or eject sample from the syringe.

The release has a cocked position and a released position. In its cocked position, the release limits the movement of the plunger driver so that sample cannot be completely ejected from the syringe. The amount of sample in the syringe at the plunger limit determines the volume of sample available for injection. Movement of the plunger driver is not so limited when the release is moved to its released position so that the desired sample volume can be injected.

Movement of the release from its cocked position to its released position is forced by the actuator. As the actuator is moved toward the release, the spring is loaded (deformed so that it applies an increased counterforce). The counterforce places the drive forces required of the operator in a range appropriate for manual control. This enhances repeatability over instances and users. With little or no training, operators can learn to apply an amount of force optimized for achieving a clean spit injection.

Once the release has been moved past its released position by the actuator, the plunger driver motion is no longer limited by the release. The spring then urges the syringe holder toward the plunger driver. This forces the plunger fully into the syringe so that sample is injected.

At the point where the actuator contacts the release, the degree of spring deformation, and thus the counterforce applied by the spring, is always the same. Thus, the initial force applied by the spring to inject the sample is highly repeatable. For embodiments in which the spring provides the entire force for sample injection, injection velocity is maximally repeatable. For embodiments in which the injection force is provided in part by the spring and in part manually, the contribution of the spring serves to enhance repeatability relative to a completely manual injection.

In a preferred realization of the invention, as the release moves from its cocked position to its released position, it forces the plunger in the sample-input direction (up) a short distance. This causes sample to be withdrawn from the needle outlet. Thus, upon release, the plunger has room to accelerate to the desired clean-spit velocity even when the sample volume to be injected is very small.

The actuator is preferably part of an interface for the sample injection port. This interface ensures alignment of the syringe needle and the injection septum. The interface is movably engaged (preferably slideably engaged) with the syringe holder. The interface can also provide for holding a sample vial during input of a sample to a syringe.

The plunger driver preferably includes a sample volume-adjust assembly. This assembly can include a rod with teeth, a disk with a scalloped rim and a threaded central aperture, and a spring-mounted shaft. The disk is held at a fixed elevation relative to the plunger driver, while the toothed rod sets the limit of plunger driver movement relative to the syringe holder (e.g., by contacting the cocked release in the limit position). In turn, the elevation of the volume-adjust rod relative to the disk sets the insertion limit of the plunger in the syringe. Thus, moving the toothed rod relative to the disk adjusts the sample volume.

The spring-mounted rod urges the disk threads against the teeth of the rod. The spring-mounted shaft engages the scalloping of the disk rim to provide volume-adjust detents. These detents resist inadvertent changing of the sample volume setting and provide discrete settings so that set volumes are repeatable. The disk can be rotated manually (overcoming the resistance of the spring-mounted shaft against the detents) so that the volume-adjust rod moves vertically, effecting fine volume adjustment. The disk can be pushed directly against the force of the spring so that the threads and teeth disengage. This allows the toothed rod to translate freely relative to the disk for gross volume adjustments.

The invention provides for the following method. After initial steps of setting the sample volume, drawing sample into the syringe, removing bubbles from the sample, cocking the release, and setting the plunger driver against the release, the sample injector is mounted on an injection port. Preferably, the port interface is shaped with respect to the port so that the sample injector is guided into proper alignment with a sample injection septum in the process at engagement. Upon engagement, the user's hand is holding the syringe holder, while an index finger is applying slight downward pressure against the plunger driver to maintain it against the cocked release.

Then the user makes a downward motion of the plunger driver, which, in turn, forces the syringe holder to deform the spring. The motion causes the syringe needle to penetrate the injection port septum. Just as the needle reaches the proper vertical position in the injection port, the actuator moves the release lever, first to its pullback position and then to its release position. On the way to its pullback position, the release forces the plunger driver up so that sample is drawn in from the needle end.

Once release is achieved, the spring urges the syringe holder up toward the plunger driver so that the sample is injected into the port and the needle begins to exit the port. Depending on the realization of the invention, the plunger driver can remain stationary or move (e.g., in response to finger-applied force) toward the syringe holder during injection. The sample pullback effected prior to release assures that the sample has sufficient room to accelerate to the clean-spit velocity. The user then lifts the sample injector off the port with the aid of the spring, completing the injection method.

A major advantage of the invention is that it converts a gross motion of a user's hand to a series of precise manipulations of a syringe, resulting in a clean-spit of a preset sample volume into an injection port. The single downward hand motion results in: 1) penetration of the septum by the needle; 2) pullback of sample from the needle end; and 3) at least partially spring driven injection of the sample. As this sequence is effected by a simple continuous hand movement, the syringe needle is in the injection port for a short enough time (less than one-half second) that the needle does not heat enough for its contents to vaporize. The simple gross motion required by the present invention contrasts with the difficult combination of a gross hand movement for the syringe and a delicate digit movement for a plunger in a conventional manual injection technique.

The spring serves both to calibrate the user's motion, moderating differences between users and injections, and to provide for a clean-spit injection—avoiding both drooling and overspitting. The pullback imposed by the release ensures there is room to accelerate to the clean-spit velocity (and this applies for both manual and automated realizations of the invention). Accordingly, optimal injection of even small sample volumes can be achieved so that, in turn, more effective component separations can be achieved using capillary gas chromatography. These and other features and advantages of the invention are detailed below with reference to the following drawings.

In planar FIGS. 3, 4, 6, 8–10, "vertical" is parallel to the length of the page, "longitudinal" is parallel to the width of the page, and "transverse" is perpendicular to the page. In some figures, some components are omitted for clarity.

DESCRIPTION OF THE PREFERRED EMBODIMENTS

Figure 1:
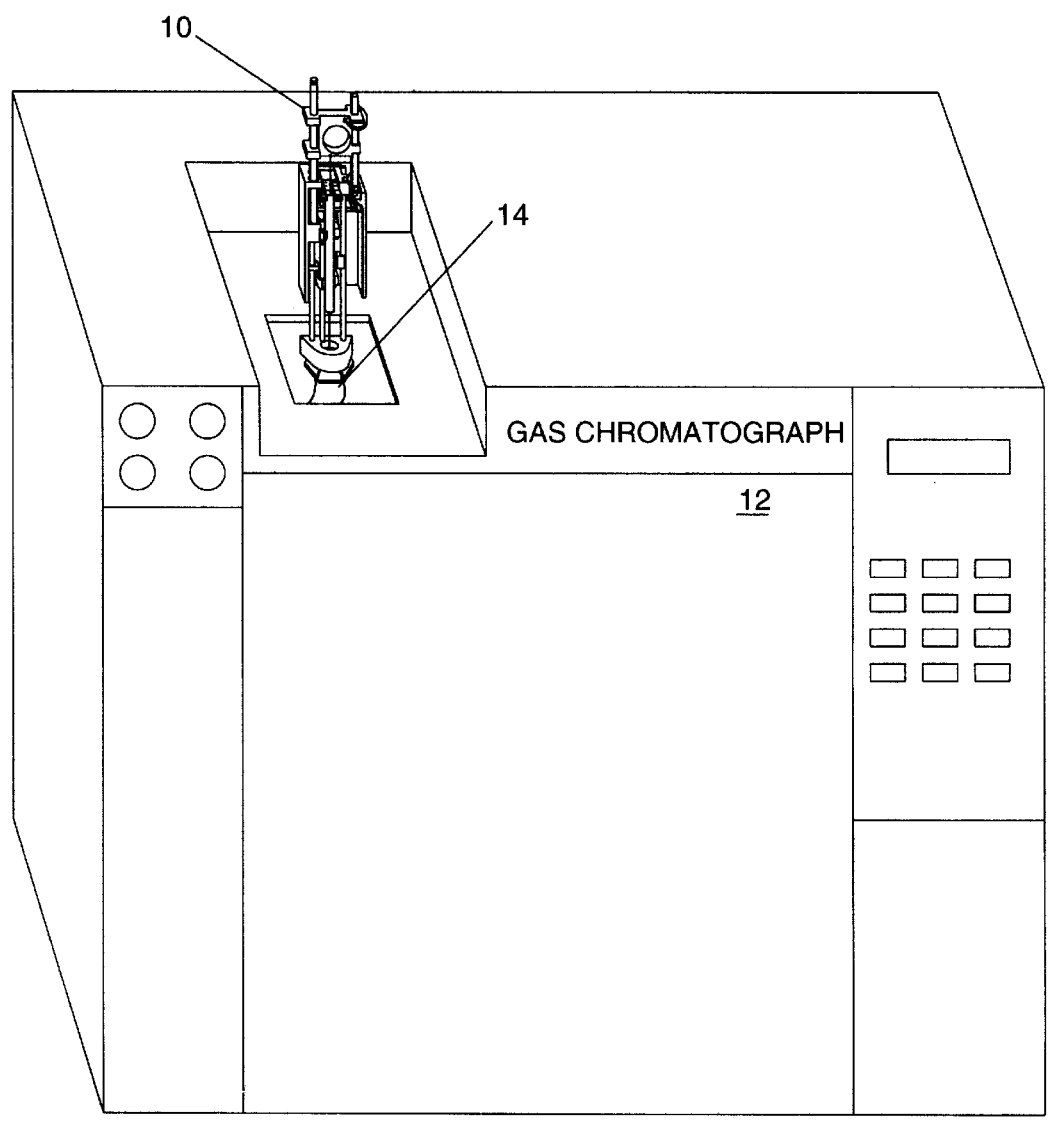
FIG. 1 is a schematic perspective illustration of a manual sample injector in accordance with the present invention mounted in position for sample injection on a gas chromatograph.
Figure 2:
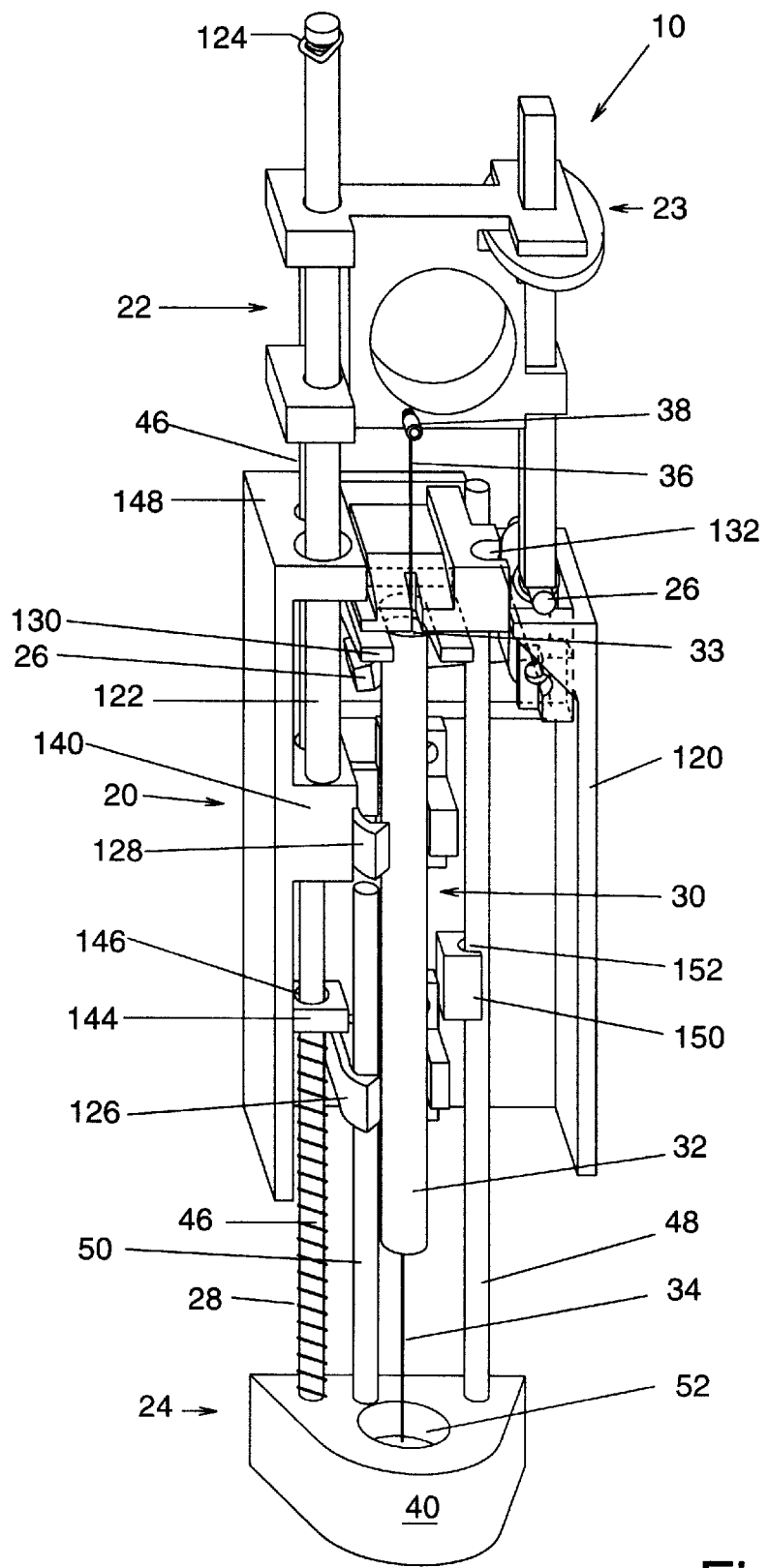
FIG. 2 is a schematic perspective view of the manual sample injector of FIG. 1.

A manual sample injector 10 in accordance with the present invention is designed for manual injection of a sample into a gas chromatograph 12 via the latter's injection port 14, as shown in FIG. 1. Sample injector 10 includes a syringe holder 20, a plunger driver 22 including a volume-adjust assembly 23, an injection port interface 24, a release lever 26, and a spring 28, as shown in FIG. 2. Injector 10 is designed for use with a syringe 30 having a body 32 with a flange 33, a needle 34, and a plunger 36. Plunger 36 has a grip 38 (best shown in FIG. 3) at a distal end that is essentially a cylinder with a narrow segment ("neck") along its height.

Syringe holder 20 holds syringe body 32 and thus needle 34 in a fixed position relative to holder 20. Plunger driver 22 engages grip 38 to hold plunger 36 in a fixed position relative to plunger driver 22. Plunger driver 22 is slideably engaged with syringe holder 20 so that plunger 36 can be moved relative to syringe body 32 as sample is introduced into and ejected from syringe 30.

Figure 3:
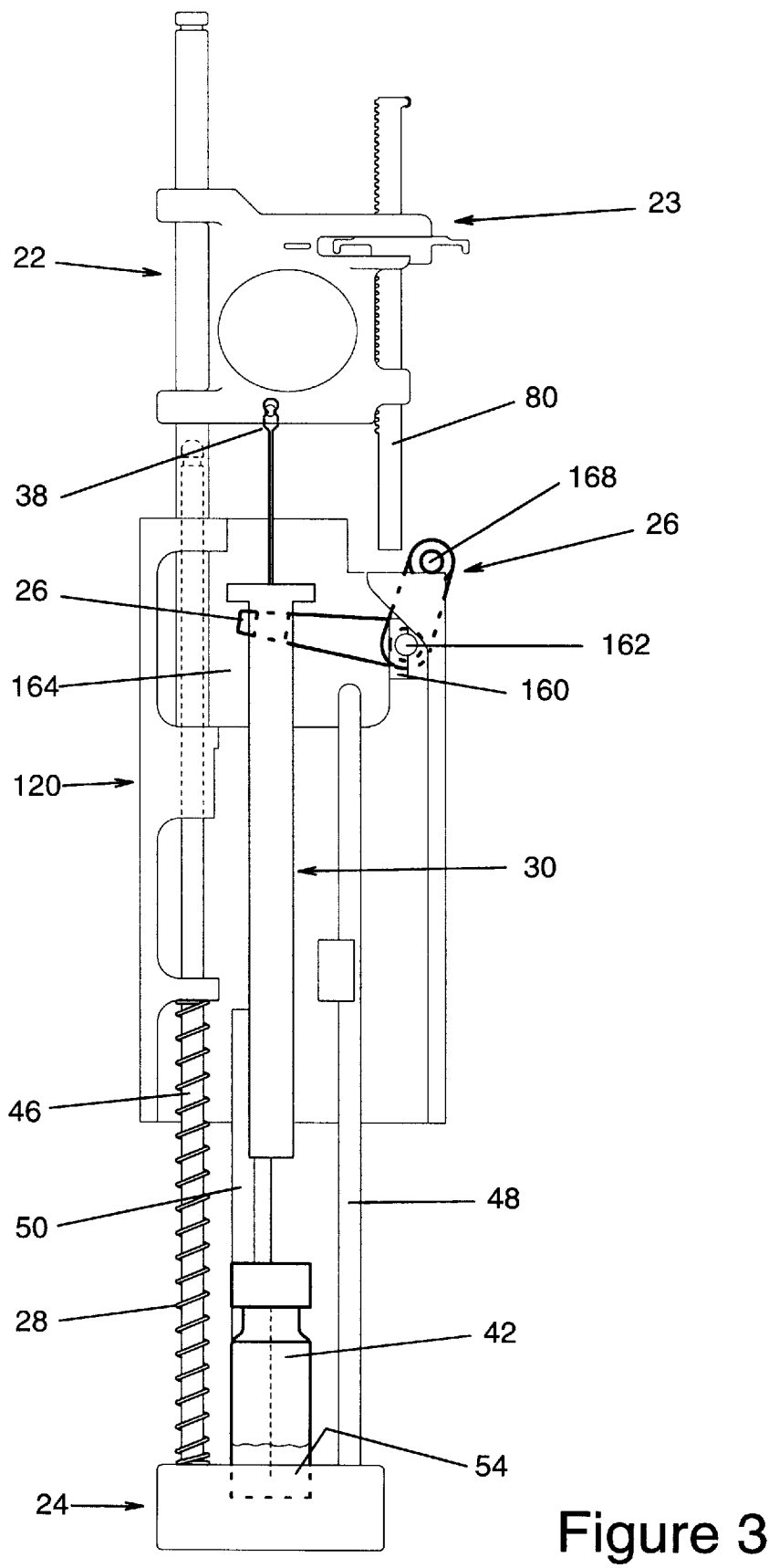
FIG. 3 is a schematic illustration of the manual sample injector of FIG. 2 with a sample vial in position for filling the syringe.
Figure 4:
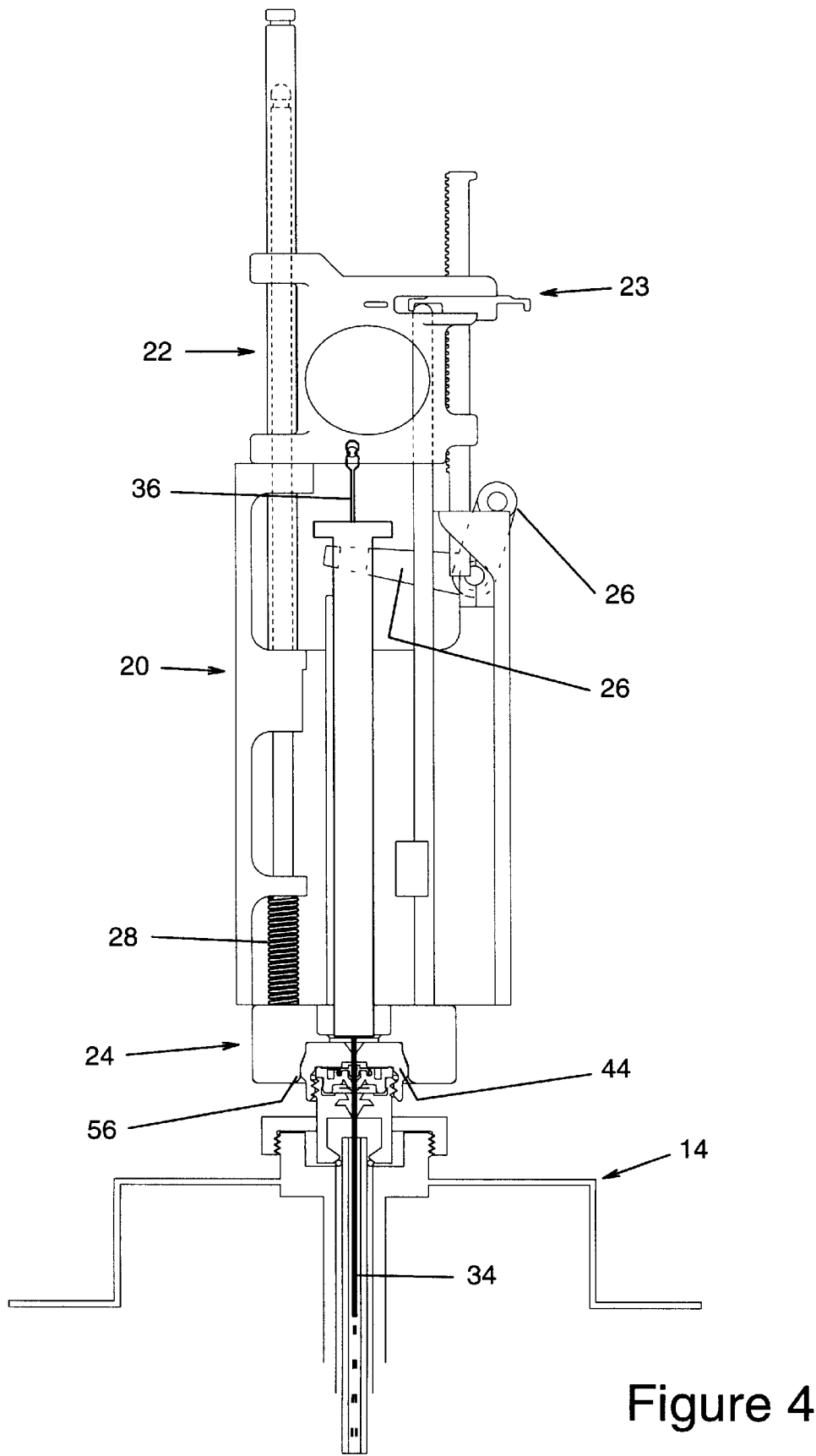
FIG. 4 is a schematic illustration of the manual sample injector of FIG. 2 mounted on an injection port of the gas chromatograph of FIG. 1 during sample injection.

Injection port interface 24 comprises guide cone 40, guide rods 46 and 48, and an actuator 50, which is also a rod. Guide cone 40 has a vertical aperture 52 to permit syringe needle 34 to extend therethrough. Cone 40 has a top depression 54 for accommodating the base of a sample vial 42, as shown in FIG. 3, and a bottom depression 56 for accommodating a septum nut 44, as shown in FIG. 4. Bottom depression 56 is conical to help guide cone 40 onto septum nut 44 during mounting. Depressions 54 and 56 are coaxial with needle aperture 52. Port interface 24 is slideably engaged with syringe holder 20 so that syringe body 32 and needle 34 can be moved toward and from vial 42 (FIG. 3) and injection port 14. In the absence of a drive force, syringe holder 20 and injection port interface 24 are urged apart by spring 28, as shown in FIG.3.

Release lever 26 is pivotally attached to syringe holder 20 so that it can rotate between a cocked position, shown in FIG. 2, and a released position, shown in FIG. 3. When release lever 26 is in its cocked position, it limits movement of plunger driver 22 relative to syringe holder 20 so that plunger 36 cannot fully eject the sample in syringe 30. The volume of syringe body 32 into which plunger 36 is prevented from extending corresponds to the sample volume to be injected into gas chromatograph 12. This volume is adjustable by volume adjust assembly 23. When release lever 26 is moved to its released position, plunger 36 can be extended completely into syringe body 32, injecting sample into injection port 14 in the process, as indicated in FIG. 4.

Figure 5:
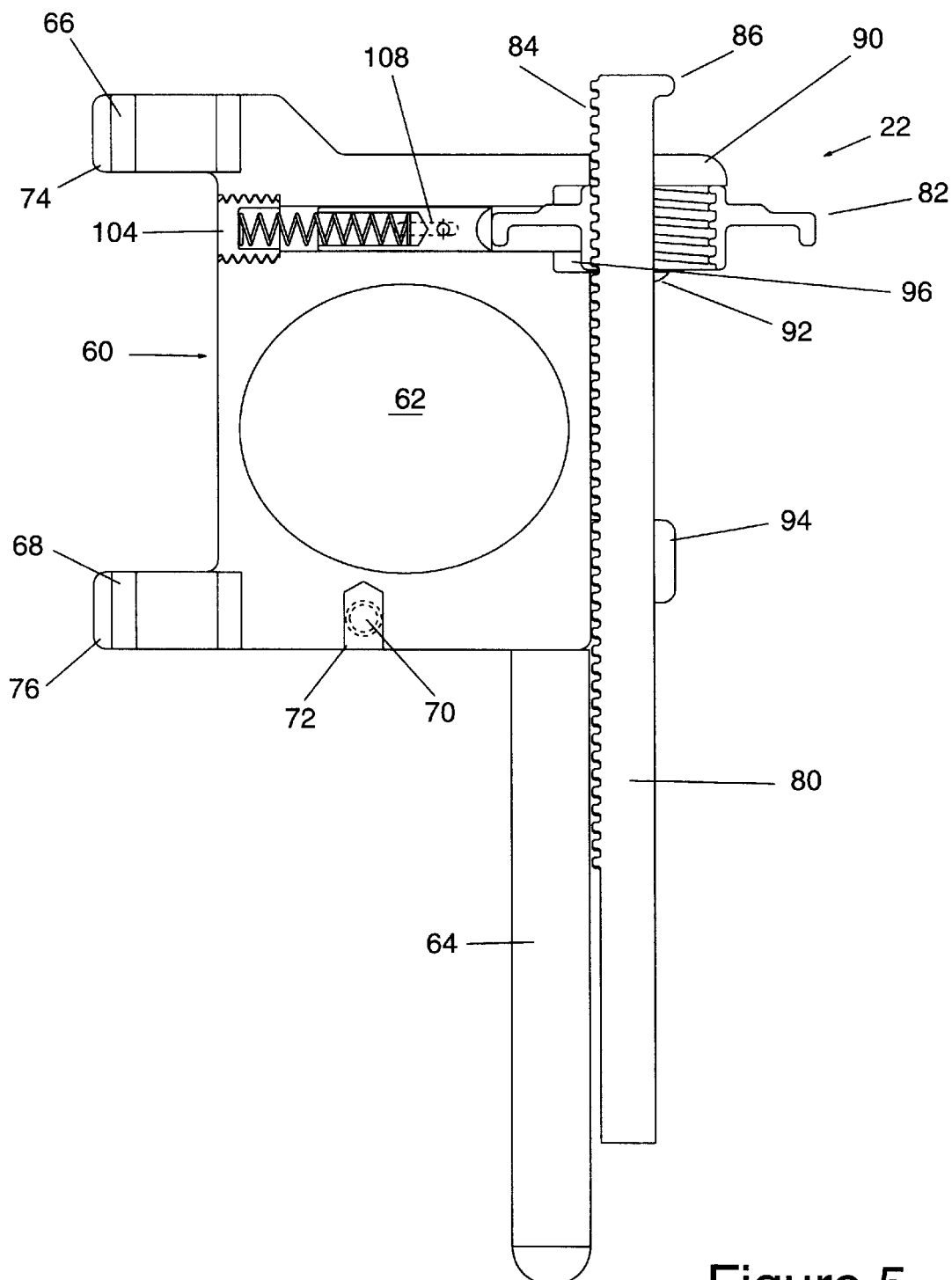
FIG. 5 is a schematic illustration of a volume-adjust assembly of the plunger driver of FIG. 2.

Plunger driver 22 comprises a plunger ring 60 defining a finger aperture 62, a guide rod 64, bushings 66 and 68, and a plunger retaining bolt 70, as shown in FIG. 5. Plunger ring 60 is roughly rectangular element. A transversely extending cylindrical aperture 62 accommodates a human finger that supplies the downward force required for sample injection.

Plunger ring 60 includes a vertical plunger-grip aperture 72 at its base for receiving plunger grip 38. An intersecting horizontal threaded aperture accommodates plunger-retaining bolt 70. Bolt 70 secures plunger grip 38 within vertical aperture 70 by contacting the neck of grip 38.

Guide rod 64 is pressed into a depression at the base of plunger ring 60. Bushings 66 and 68 are press fitted respectively into hollow cylindrical protrusions 74 and 76 of plunger ring 60. Bushings provide for low friction sliding of plunger driver 22 relative to syringe holder 20. Other features of plunger driver 22 are described in connection with volume adjustment assembly 23.

Volume-adjust assembly 23 includes a volume-adjust rod 80 and a volume-adjust disk 82. Volume-adjust rod 80 is essentially an elongated rectangular parallelepiped, being longer in the longitudinal dimension than in the transverse dimension. The side facing finger aperture 62 has teeth 84 along most of its vertical extent. There is a small ledge 86 extending away from finger aperture 62 that serves as a stop. Plunger ring 60 includes upper, middle, and lower shaft-guide protrusions 90, 92, and 94 with respective rectangular apertures that guide volume-adjust rod 80 in its relative vertical movement therethrough without engaging teeth 84.

Figure 6:
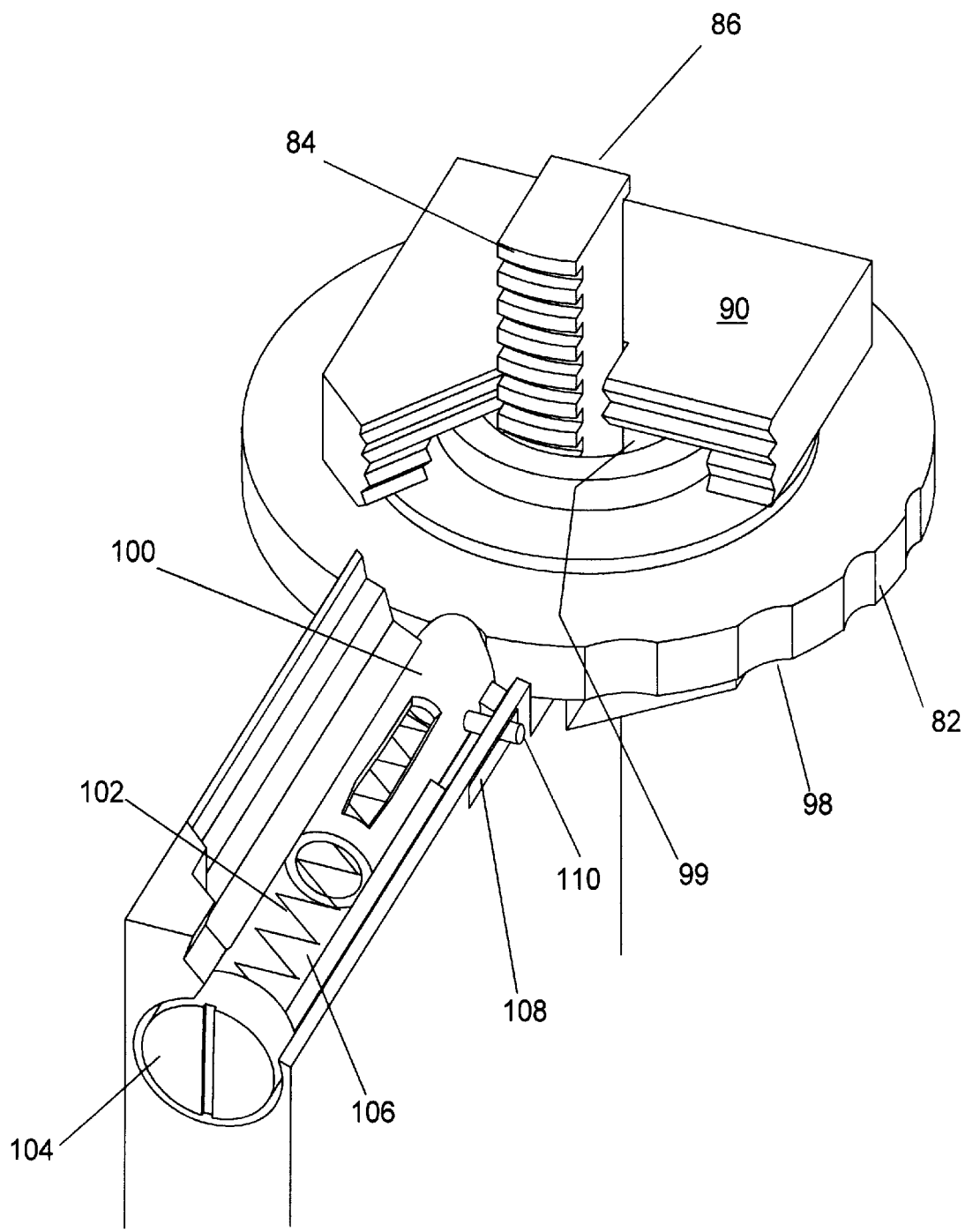
FIG. 6 is a partial cutaway schematic illustration of a plunger driver of the injector of FIG. 2.

Upper shaft-guide protrusion 90 and middle shaft-guide protrusion 92 also serve as the upper and lower walls respectively of a slot 96 that accommodates volume-adjust disk 82. Disk 82 has a scalloped rim 98 and a threaded aperture 99, as shown in FIG. 6. Volume-adjust rod 80 extends through aperture 99, which is large enough to accommodate rod 80 without the latter's teeth 84 engaging the former's threads.

Teeth 84 do engage the threads of disk aperture 99 when disk 82 is urged against rod 80 by a longitudinally extending disk-engagement shaft 100 that has a head designed to engage the scalloped detents of disk 82. Disk-engagement shaft 100 is urged against disk 82 by a disk-engagement spring 102. Spring 102 is held in place by spring cap 104 threaded into a longitudinal disk-engagement aperture 106 through plunger ring 60. Aperture 106 accommodates not only spring cap 104, but also spring 102, and rod 100.

Plunger ring 60 has a "limit" aperture 108 that extends transversely through plunger ring 60 so as to intersect disk-engagement aperture 106. Limit aperture 108 accommodates a small-diameter "limit" pin 110 that also extends through a mating aperture on disk-engagement rod 100. The cross section of limit aperture 108 is elongated in the longitudinal direction to permit longitudinal movement of limit pin 110, and thus of disk-engagment rod 100 toward and away from volume-adjust rod 80. This arrangement allows a user to disengage teeth 84 from the threads of disk 82 by pushing disk 82 longitudinally toward finger aperture 62. Accordingly, gross volume adjustment can be made by sliding volume-adjust rod 80 with teeth 84 disengaged, while fine volume adjustments can be made by rotating disk 82 with teeth 84 engaged.

Syringe holder 20 includes metal frame 120, a guide rod 122 with a C-clip 124 attached, and three plastic syringe mounts 126, 128, and 130, as best shown in FIG. 2. Each syringe mount 126, 128, 130, is attached to the back of frame 120 by a respective pair of screws (not shown). Lower mount 126 grips syringe body 32 toward the needle end of its vertical extent. Middle mount 128 grips syringe body 32 near the middle of its vertical extent. Upper mount 130 grips syringe body flange 33. Upper mount 128 also includes a semi-cylindrical groove 132 for accommodating drive-assembly guide rod 64 (FIG. 5). Complementarily, plunger driver 22 is engaged with syringe holder guide rod 122, which extends through bushings 66 and 68 (FIG.5). Movement of plunger driver 22 is limited at one end by C-clip 124 and at the other end by the top of syringe holder frame 120.

Syringe-holder frame 120 includes a protrusion 140 that includes a threaded aperture for securing guide rod 122 and an guide aperture for guide rod 46 of injection port interface 24. Guide rod 46 has a C-clip (not shown) to keep it from falling through protrusion 140. A second protrusion 144 also has a guide aperture for guide rod 46. A top ledge 148 of frame 120 also has guide apertures for guide rods 46 and 122. The C-clip for guide rod 46 can pass through the respective aperture of ledge 148. Frame 120 also has a protrusion 150 with a groove 152 of semicircular cross section that serves as a guide for guide rod 48.

Syringe holder frame 120 has a protrusion 160 for holding a small rod that serves as a fulcrum 162 for release lever 26, as shown in FIG. 3. Frame 120 has a cutout area 164 for accommodating the actuator end of release lever 26. The blocking end of release lever 26 has a rod 168 that extends transversely therethrough. This rod 168 is the element that actually contacts volume-adjust rod 80 when injector 10 is cocked.

Figure 7:
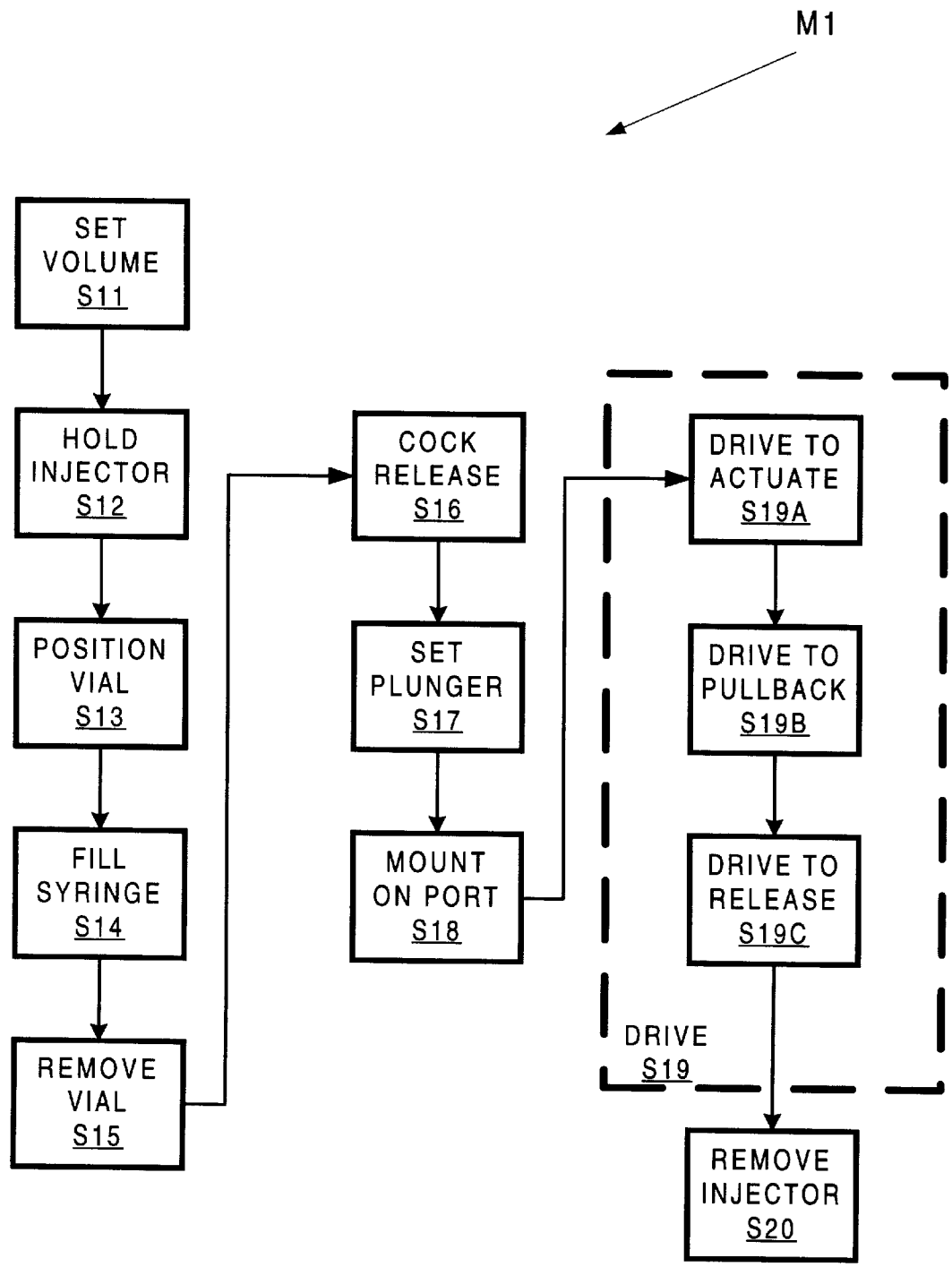
FIG. 7 is a flow chart of a method of using the manual sample injector of FIG. 2.

A method M1 of the invention practiced using manual sample injector 10 is flow charted in FIG. 7. At step S11, the sample volume is set, as needed, using volume-adjust assembly 23 (FIG. 5). Gross adjustment can be effected by sliding volume-adjust rod 80 relative to volume-adjust disk 82 and, thus, plunger ring 60. Teeth 84 of volume-adjust rod 80 are disengaged from threads of disk 82 by pushing disk 82 longitudinally against disk-engagement rod 100 so as to compress disk-engagement spring 102. For fine adjustments, disk 82 is released so that its threads engage teeth 84. Disk 82 can then be rotated so that the screw action of its threads gradually translates volume-adjust rod 80 vertically.

Step S12 involves the user's hand engaging injector 10 as follows. Syringe holder frame 120 (FIG. 2) is gripped by a thumb and three fingers, while the index finger extends through finger aperture 62. For a right-handed user, the left hand can engage injector 10, leaving the right hand free for other tasks. A left-handed user can hold injector 10 with the right hand.

Step S13 involves positioning sample vial 42 (FIG. 3) in the upper depression 54 of guide cone 40. Step 14 involves filling syringe with sample to a level at or, preferably, above that corresponding to the preset sample volume. With release lever 26 in its released position, as in FIG. 3, the index finger can force plunger driver 22 to its full ejection position. The user's hand can then move plunger driver 22 and syringe holder 20 down until syringe needle 34 extends through the sample vial septum so that the needle opening is within the volume of sample. The index finger pulls plunger driver 22 up until syringe 30 is filled beyond the level corresponding to the desired volume of sample to be injected. At step S15, sample vial 42 is removed. Before or after this step, plunger driver 22 can be operated so that plunger 36 can be pumped with syringe 30 inclined with needle 34 inclined upward to remove air trapped in the sample.

Figure 8:
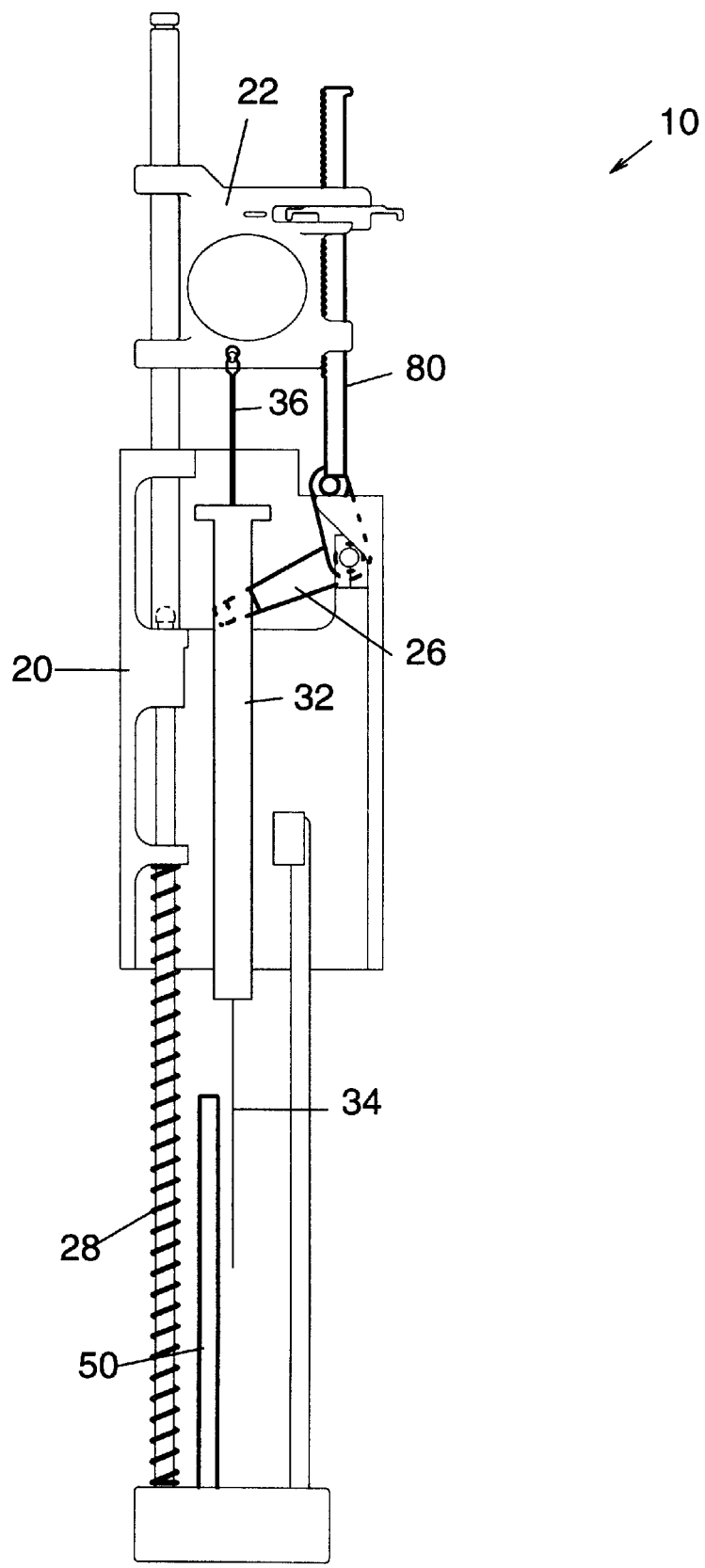
FIG. 8 is a schematic illustration of the manual sample injector of FIG. 2 cocked and fully open.

At step S16, release lever is moved to its cocked position, as shown in FIG. 8. At step S17, plunger driver 22 is pushed so that volume-adjust rod 80 meets release lever 26. This inserts plunger 36 so that excess sample is discharged, retaining only the volume of sample desired for injection. At step S18, sample injector 10 is mounted on port 14 so that the latter is engaged by interface 24.

At step S19, the user pushes plunger driver 22 (with the index finger) and thereby syringe holder 20 toward injection port 14 against the resistance of spring 28. Reflexively, the user increases the applied force as the spring's resistance gradually increases as it compresses. After sample is injected into port 14, the user lifts sample injector 10 partly in response to a hard stop as syringe holder 20 and plunger driver 22 reach limit position, and also as spring 28 urges syringe holder 20 upward. Needle 34 is thus removed from port 14, and sample injector 10 is lifted from port 14, completing sample injection method M1.

Figure 9:
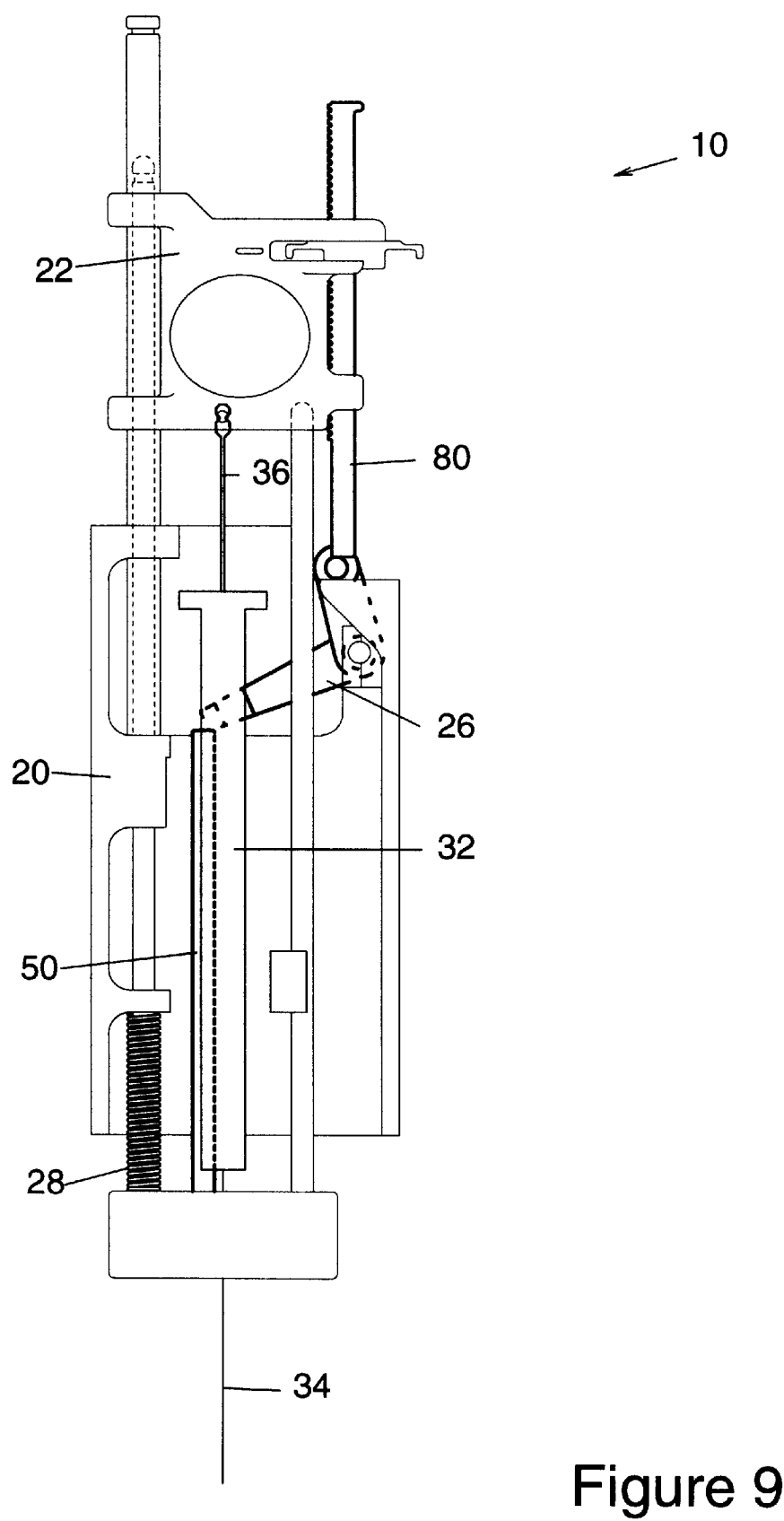
FIG. 9 is a schematic illustration of the manual sample injector of FIG. 2 with an actuator beginning to move a release from its cocked position to its pullback position.

The gross downward arm movement of step S19 is converted to a series of actions on the part of injector 10. Substep S19A involves moving syringe holder 20 and plunger driver 22 down so that needle 34 is inserted into port 14, as indicated in FIG. 9. Substep 19A continues until actuator 50 contacts release lever 26.

Figure 10:
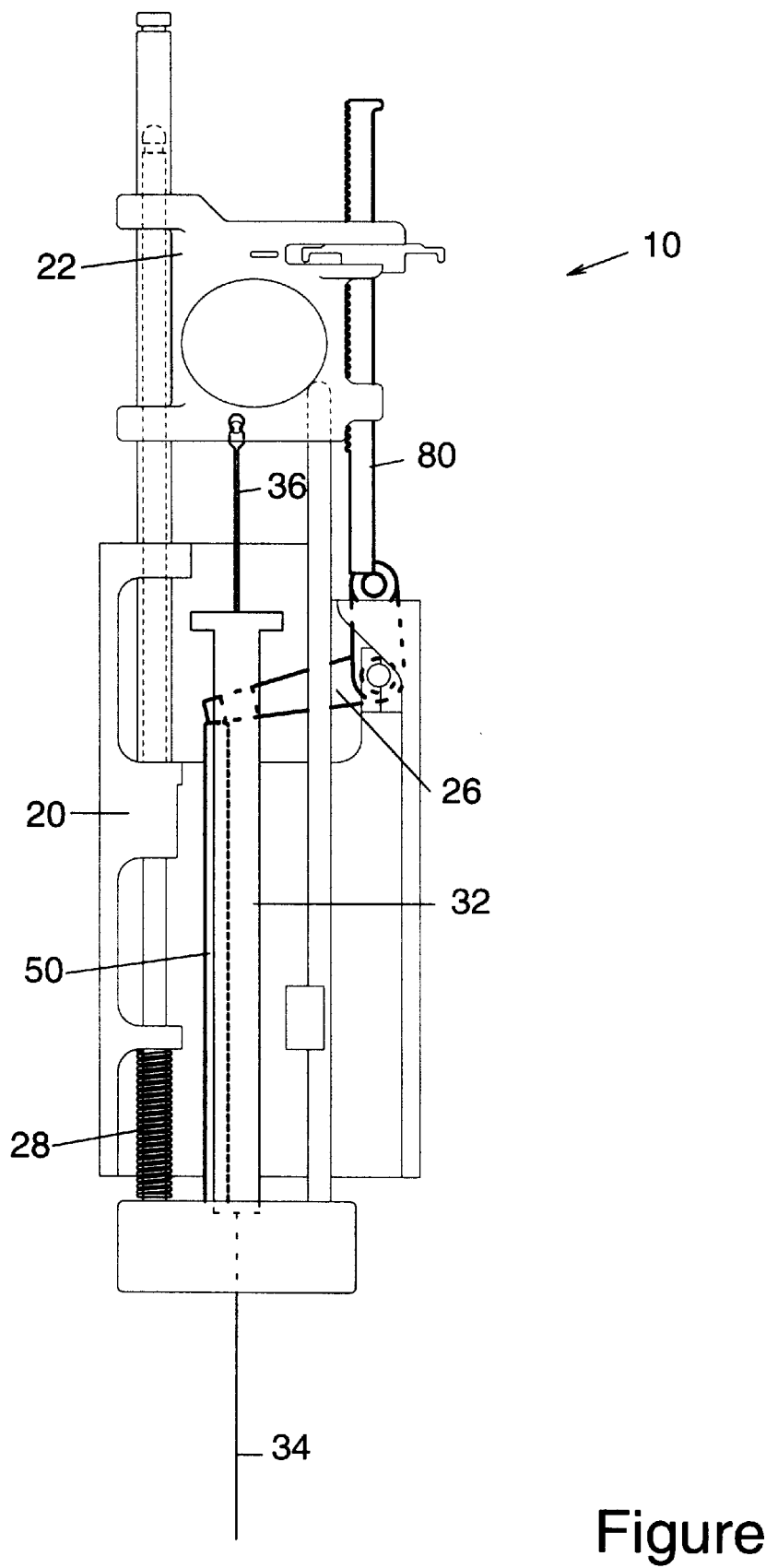
FIG. 10 is a schematic illustration of the manual sample injector of FIG. 2 with its release in the pullback position.

Substep 19B involves further downward movement of syringe holder 20 so that actuator 50 forces release lever 26 to rotate to its pullback position, as indicated in FIG. 10. This forces volume-adjust rod 80 up relative to syringe holder 20 so that plunger 36 withdraws sample from the tip of needle 34. The distance that sample is withdrawn is selected to permit sufficient sample acceleration before leaving needle 34 to achieve the clean-spit velocity.

Substep 19C involves further downward arm motion and further action on the part of actuator 50 to rotate release lever 26 to its released position so that it no longer limits the motion of volume-adjust rod 80. Thus, spring 28 forces syringe holder 20 up and the user's finger forces plunger driver 22 down so that the sample is injected into port 14, as indicated in FIG. 4.

The sample injection is the result of plunger driver 22 and plunger 36 moving to the full sample ejection position relative to syringe holder 20 and syringe body 32. This relative motion involves the syringe holder moving upward due to the force provided by spring 28. Concurrently, plunger driver 22 is moved downward under finger pressure.

In an alternative embodiment, the plunger driver is held at a fixed position upon release. In this case, the energy-storage spring provides all the energy used for sample injection. This embodiment removes variations in sample velocity due to variations by a user over time or differences between users. However, a nonlinear spring is used to minimize differences in injection velocity due to the different distances over which acceleration can occur for different sample volumes. In the illustrated embodiment, a practical tradeoff is made between user variability due to finger-driven motion of the plunger and volume-variability due to differences in the degree of spring decompression.

The described embodiments use a helical spring. Springs of bent or twisted resilient material can also be used. In addition, other types of springs such as cylinders of compressed air can be used to provide the counterforce for sample injection.

The present invention provides for many alternatives to the described embodiment. Alternative arrangements can be made for adjusting the sample volume. For example, the sample adjustment assembly can be part of the syringe holder instead of the plunger driver. likewise, there are mechanical alternatives to the disclosed release lever. These and other variations upon and modifications to the described embodiments are provided for by the present invention, the scope of which is defined by the following claims.

What is claimed is:

1. A sample injector comprising:

a syringe holder assembly for holding a syringe body in a fixed position relative thereto;

a plunger driver for holding a plunger of said syringe in a fixed position relative thereto, said plunger driver being movably engaged with said syringe holder so that said plunger moves relative to said syringe as said plunger driver is moved relative to said syringe holder;

a release having a cocked position and a released position, said release in its released position allowing said plunger driver to move relative to said syringe holder so that said plunger can achieve a full ejection position relative to said syringe, said release when in its cocked position limiting movement of said plunger driver relative to said syringe holder so that said plunger is maintained at least a predetermined minimum distance from said full ejection position;

an interface assembly for engaging a sample injection port so that sample ejected from said syringe enters said sample injection port, said interface assembly being movably engaged with said syringe holder so that said syringe can move relatively toward and away from said sample injection port, said interface assembly having an actuator that, when said release is in its cocked position and said syringe is moving toward said port, moves said release from its cocked position to its released position; and a spring for providing a force opposing motion of said actuator toward said release due to motion of said syringe holder relative to said interface assembly.

2. A sample injector as recited in claim 1 wherein said release has an intermediate position between said cocked position and said released position at which said release limits movement of said plunger driver relative to said syringe holder so that said plunger is moved from said predetermined minimum distance to a pullback distance greater than said predetermined minimum distance as said actuator moves said release from its cocked position to its released position.

3. A sample injector as recited in claim 1 wherein said plunger driver includes means for receiving a human finger which thus can supply a force opposing a force supplied by said spring means so that said actuator moves said release from its cocked position to its released position.

4. A sample injector as recited in claim 1 further comprising adjustment means for adjusting said minimum distance.

5. A sample injector as recited in claim 4 wherein said adjustment means is coupled to said drive means and is movable relative thereto.

6. A sample injector as recited in claim 5 wherein said adjustment means is in contact with said release when said release is in its cocked position.

* * * * *